(12) United States Patent
Olson

(10) Patent No.: US 9,278,226 B2
(45) Date of Patent: Mar. 8, 2016

(54) SHOCK THERAPY FOR MONOMORPHIC DETECTED VENTRICULAR TACHYCARDIA

(71) Applicant: Medtronic, Inc., Minneapolis, MN (US)

(72) Inventor: Walter H Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 41 days.

(21) Appl. No.: 14/198,058

(22) Filed: Mar. 5, 2014

(65) Prior Publication Data

US 2015/0251012 A1    Sep. 10, 2015

(51) Int. Cl.
*A61N 1/39*   (2006.01)

(52) U.S. Cl.
CPC ............ *A61N 1/3906* (2013.01); *A61N 1/3962* (2013.01); *A61N 1/3975* (2013.01); *A61N 1/3987* (2013.01)

(58) Field of Classification Search
CPC ........................... A61N 1/3962; A61N 1/3622
USPC ................................................ 607/4, 14, 5, 9
See application file for complete search history.

(56) References Cited

U.S. PATENT DOCUMENTS

| | | | |
|---|---|---|---|
| 5,193,535 | A | 3/1993 | Bardy et al. |
| 5,354,316 | A | 10/1994 | Keimel |
| 5,439,483 | A | 8/1995 | Duong-Van |
| 5,447,519 | A * | 9/1995 | Peterson ........................... 607/5 |
| 5,545,186 | A | 8/1996 | Olson |
| 5,855,593 | A | 1/1999 | Olson |
| 6,236,882 | B1 | 5/2001 | Lee |
| 6,393,316 | B1 | 5/2002 | Gillberg |
| 7,130,677 | B2 | 10/2006 | Brown |
| 7,181,276 | B1 * | 2/2007 | Province et al. .................. 607/7 |
| 7,742,812 | B2 | 6/2010 | Ghanem |
| 8,160,684 | B2 | 4/2012 | Ghanem |
| 8,170,663 | B2 | 5/2012 | DeGroot |
| 8,332,022 | B2 | 12/2012 | Brown |
| 8,401,629 | B2 | 3/2013 | Stadler |
| 8,532,785 | B1 | 9/2013 | Crutchfield |
| 2003/0023273 | A1 * | 1/2003 | DeGroot et al. .................. 607/4 |

(Continued)

FOREIGN PATENT DOCUMENTS

| | | |
|---|---|---|
| EP | 2 674 194 A2 | 12/2013 |
| WO | WO 2005/097258 A1 | 10/2005 |

OTHER PUBLICATIONS (PCT/US2015/017225) PCT Notification of Transmittal of the International Search Report and the Written Opinion of the International Searching Authority.

*Primary Examiner* — Carl H Layno
*Assistant Examiner* — Erin M Piateski
(74) *Attorney, Agent, or Firm* — Michael J. Ostrom

(57) ABSTRACT

An implantable medical device system detects and treats monomorphic ventricular tachycardia (VT). The system includes a sensing module for receiving a cardiac signal and a therapy delivery module including a capacitor and an output circuit. A control module is coupled to the sensing module and the therapy delivery module and is configured to detect a tachycardia from the cardiac signal and initiate charging of the capacitor in response to detecting the tachycardia. The control module performs a method for simultaneously monitoring a voltage on the capacitor and a morphology of the cardiac signal during the charging and controls the therapy delivery circuit to deliver a shock pulse at less than a programmed shock energy in response to both the voltage reaching at least a minimum voltage and the morphology being monomorphic.

24 Claims, 8 Drawing Sheets

(56) References Cited

U.S. PATENT DOCUMENTS

| | | | |
|---|---|---|---|
| 2003/0204210 A1* | 10/2003 | Ousdigian et al. | 607/14 |
| 2005/0251217 A1* | 11/2005 | Brown | 607/14 |
| 2007/0016257 A1* | 1/2007 | Brown et al. | 607/5 |
| 2013/0030481 A1* | 1/2013 | Ghosh et al. | 607/14 |

* cited by examiner

SHOCK THERAPY FOR MONOMORPHIC DETECTED VENTRICULAR TACHYCARDIA

TECHNICAL FIELD

The disclosure relates generally to implantable medical devices and, in particular, to an apparatus and method for delivering a therapy for terminating monomorphic ventricular tachycardia.

BACKGROUND

Implantable medical devices are available for treating cardiac tachyarrhythmias by delivering anti-tachycardia pacing therapies and electrical shock therapies for cardioverting or defibrillating the heart. Such a device, commonly known as an implantable cardioverter defibrillator or "ICD", senses electrical activity from the heart, determines a patient's heart rate, and classifies the rate according to a number of heart rate zones in order to detect episodes of ventricular tachycardia or fibrillation. Typically a number of predefined rate zones are defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into defined detection interval ranges are counted to provide a count of ventricular tachycardia (VT) or ventricular fibrillation (VF) intervals, for example. A programmable number of intervals to detect (NID) defines the number of tachycardia intervals occurring consecutively or out of a given number of preceding event intervals that are required to detect VT or VF.

Tachyarrhythmia detection may begin with detecting a fast ventricular rate, referred to as rate- or interval-based detection. Once VT or VF is detected based on rate, the morphology of the sensed depolarization signals, e.g. wave shape, amplitude or other features, may be used in discriminating heart rhythms to improve the sensitivity and specificity of tachyarrhythmia detection methods. For example, before a therapy decision is made, VT detection may further require discrimination between supraventricular tachycardia (SVT) and VT using cardiac signal waveform morphology analysis, particularly when a fast 1:1 atrial to ventricular rate is being sensed.

A primary goal of a tachycardia detection algorithm is to rapidly respond to a potentially malignant rhythm with a therapy that will terminate the arrhythmia with high certainty. Another goal, however, is to avoid excessive use of ICD battery charge, which shortens the life of the ICD, e.g. due to delivering unnecessary therapies or therapies at a higher voltage than needed to terminate a detected tachyarrhythmia. Minimizing the patient's exposure to painful shock therapies is also an important consideration. Accordingly, a need remains for ICDs that perform tachycardia discrimination with high specificity and control therapy delivery to successfully terminate a detected VT while conserving battery charge and limiting patient exposure to painful shocks.

DETAILED DESCRIPTION

Figure 1A:
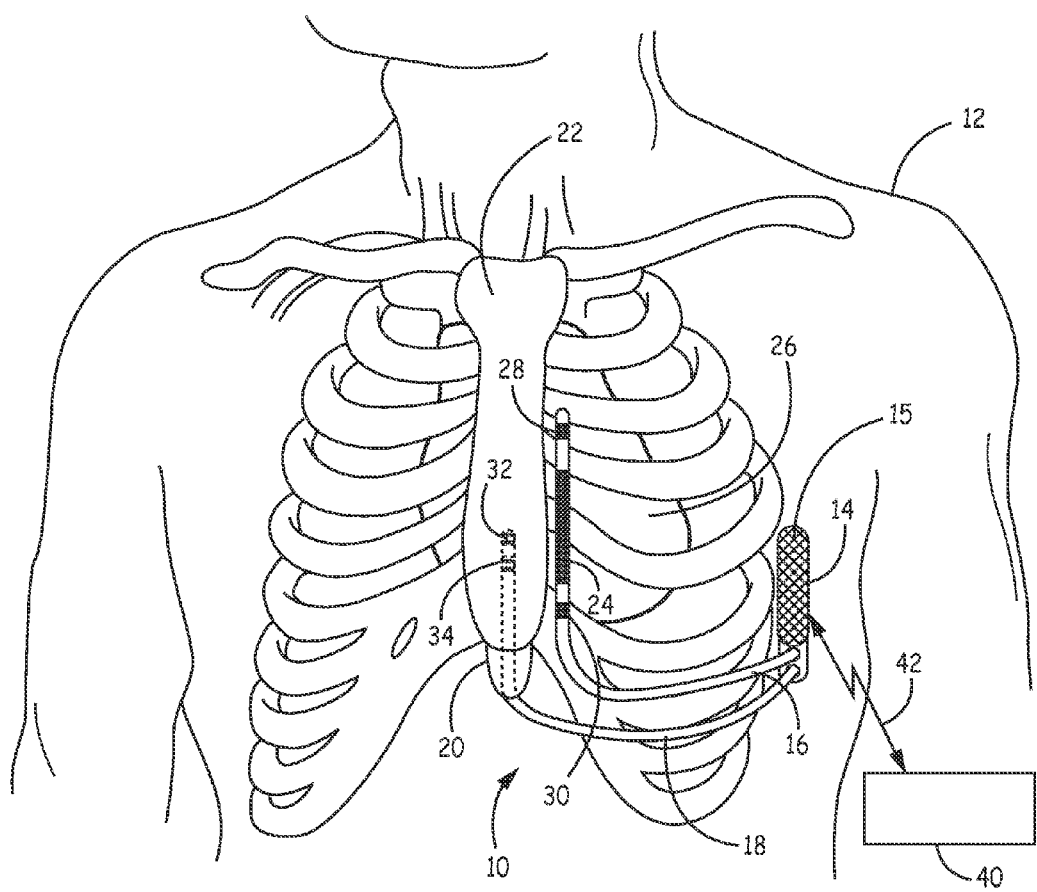
FIGS. 1A, 1B and 1C are conceptual diagrams of a patient implanted with an example IMD system.

An ICD according to the present disclosure includes a tachyarrhythmia detection module for discriminating between monomorphic and polymorphic VT. When VT or VF is detected, early therapy delivery is important in terminating a malignant, or potentially malignant, rhythm. Most spontaneous VT episodes are monomorphic, in which the depolarization waveform morphologies are highly regular, as opposed to polymorphic VT in which waveform morphologies are irregular. Monomorphic VT is tachycardia that originates in the ventricular chambers (as opposed to being conducted from the atria) and characterized by the morphological appearance of the electrocardiogram (ECG) on all heart beats matching each other in both amplitude and wave shape (e.g. R-wave width, slope, contour, number of peaks, number of inflection points, etc.). Polymorphic VT is tachycardia that originates in the ventricular chambers but the ECG morphological appearance varies from beat to beat (in amplitude, wave shape or both). VF is similar to polymorphic VT with highly variable amplitudes and wave shapes but often lower amplitudes and higher rates. Ventricular flutter is a very fast type of VF with regular sinusoidal wave shapes with no isoelectric (flat line) line between the R-wave depolarizations and requires high energy shocks to terminate. As described below, morphological analysis of the ECG comparing the wave shape from a series of heart beats is used to discriminate between monomorphic and polymorphic VT.

The RR intervals occurring during monomorphic VT and polymorphic VT can be similar. Rate-based discrimination of monomorphic and polymorphic VT is not always reliable. Yet, monomorphic VT can typically be terminated with a lower shock energy than polymorphic VT. If not discriminated from each other, excessive shock energy may be delivered to terminate a monomorphic VT since a relatively high shock energy is typically programmed to terminate unspecified VT or VF with a high confidence of success.

As disclosed herein, when VT is detected by an ICD, the ICD control module initiates charging of high voltage (HV) capacitors in preparation for delivering a cardioversion shock at a programmed shock energy. The ICD control module operates during charging of the capacitors to determine if the detected VT is monomorphic. If so, the control module terminates capacitor charging prior to reaching the voltage required to deliver the programmed shock energy, and an R-wave synchronized shock is delivered to terminate the monomorphic VT with a shock energy that is less than the programmed shock energy. If the VT is polymorphic, the capacitor charging is completed to a voltage required to deliver the full programmed shock energy.

In practice, the clinician or user typically programs the shock energy for treating VT or VF in Joules. The ICD estimates the deliverable shock energy using a measured capacitor voltage. The capacitor voltage may be referred to herein as a "programmed" voltage even though it is recognized that in most circumstances it is the shock energy in Joules that is the programmed value, not a capacitor voltage. The "programmed voltage" is the capacitor voltage that is required to deliver a corresponding programmed shock energy.

Figure 1B:
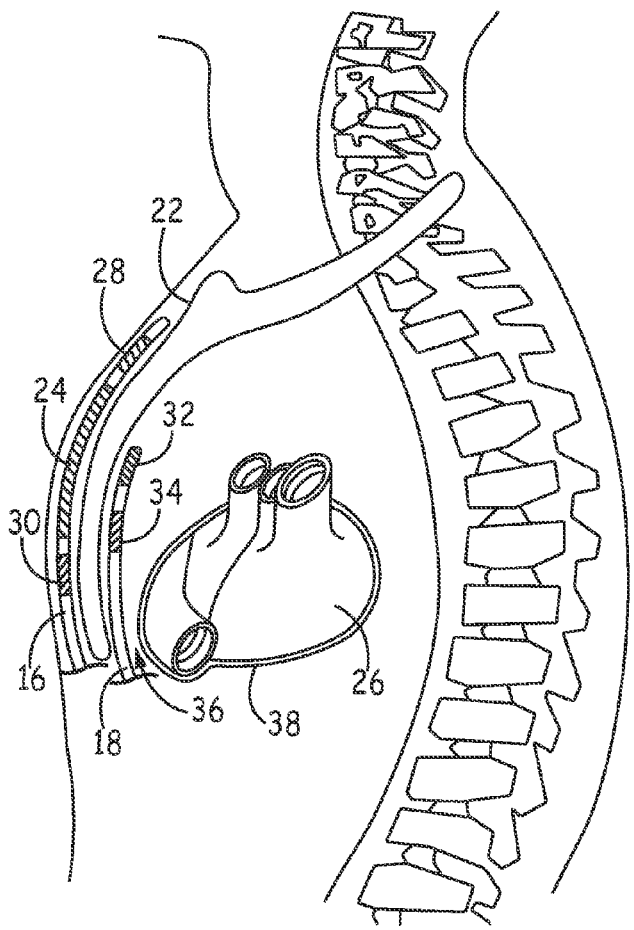
Figure 1C:
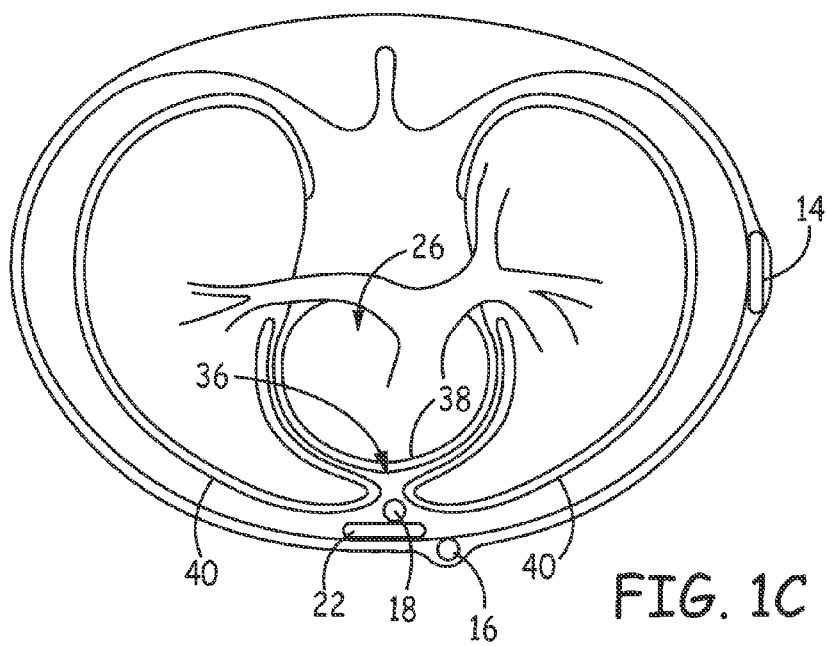

FIGS. 1A, 1B and 1C are conceptual diagrams of patient 12 implanted with an example IMD system 10' that includes a second lead 16 extending from ICD 14. FIG. 1A is a front view of patient 12 implanted with IMD 10. FIG. 1B is a side view and FIG. 1C is a transverse view of patient 12 implanted with IMD system 10. IMD system 10 includes an ICD 14 connected to a defibrillation lead 16 and a pacing lead 18. In the example illustrated in FIGS. 1A-C, ICD 14 is implanted subcutaneously on the left midaxillary of patient 12. ICD 14 may, however, be implanted at other subcutaneous locations on patient 12 as described later.

Defibrillation lead 16 includes a proximal end that is connected to ICD 14 and a distal end that includes one or more electrodes. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. The distal end of defibrillation lead 16 may be positioned near the second or third rib. However, the distal end of defibrillation lead 16 may be positioned further superior or inferior depending on the location of ICD 14 and other factors. Although illustrated as being offset laterally from and extending substantially parallel to sternum 22 in the example of FIGS. 1A-C, defibrillation lead 16 may be implanted over sternum 22, offset from sternum 22, but not parallel to sternum 22 (e.g., angled laterally from sternum 22 at either the proximal or distal end).

Defibrillation lead 16 includes a defibrillation electrode 24, which may be an elongated coil electrode, toward the distal end of defibrillation lead 16. Defibrillation lead 16 is placed such that a therapy vector between defibrillation electrode 24 and a housing or can electrode of ICD 14 is substantially through or across the ventricle(s) of heart 26.

Defibrillation lead 16 may also include one or more sensing electrodes, such as sensing electrodes 28 and 30, located toward the distal end of defibrillation lead 16. In the example illustrated in FIGS. 1A-C, sensing electrodes 28 and 30 are separated from one another by defibrillation electrode 24. ICD 14 may sense electrical activity of heart 26 via a combination of sensing vectors that include combinations of electrodes 28 and 30 and the housing or can electrode of ICD 14. For example, ICD 14 may obtain electrical signals sensed using a sensing vector between electrodes 28 and 30, obtain electrical signals sensed using a sensing vector between electrode 28 and the conductive housing or can electrode of ICD 14, obtain electrical signals sensed using a sensing vector between electrode 30 and the conductive housing or can electrode of ICD 14, or a combination thereof. In some instances, ICD 14 may even sense cardiac electrical signals using a sensing vector that includes defibrillation electrode 24.

Pacing lead 18 includes a proximal end that is connected to ICD 14 and a distal end that includes one or more electrodes. Pacing lead 18 extends subcutaneously from ICD 14 toward xiphoid process 20. At a location near xiphoid process 20 pacing lead 18 bends or turns and extends superior upward in the substernal/retrosternal space. In one example, pacing lead 18 may be placed in the mediastinum 36 and, more particularly, in the anterior mediastinum. The anterior mediastinum is bounded laterally by pleurae 40, posteriorly by pericardium 38, and anteriorly by sternum 22. Pacing lead 18 may be implanted within the mediastinum 36 such that one or more electrodes 32 and 34 are located over a cardiac silhouette of the ventricle as observed via fluoroscopy. In the example illustrated in FIGS. 1A-C, pacing lead 18 is located substantially centered under sternum 22. In other instances, however, pacing lead 18 may be implanted such that it is offset laterally from the center of sternum 22.

Although described herein as being implanted in the substernal/retrosternal space, the mediastinum, or the anterior mediastinum, leadless pacing lead 18 may be implanted in other extra-pericardial locations. In this disclosure, the term "extra-pericardial locations" refers to locations in the region around, but not in contact with, the outer heart surface. The region defined as the extra-pericardial includes the gap, tissue, bone, or other anatomical features around the perimeter of, and adjacent to, but not in contact with the pericardium. These may include the superior mediastinum, middle mediastinum, posterior mediastinum, in the sub-xiphoid or inferior xiphoid area, near the apex of the heart, or other location not in intimate contact with the heart and not subcutaneous.

Pacing lead 18 includes electrodes 32 and 34 located near a distal end of pacing lead 18. Electrodes 32 and 34 may comprise ring electrodes, hemispherical electrodes, coil electrodes, helix electrodes, or other types of electrodes, or combination thereof. Electrodes 32 and 34 may be the same type of electrodes or different types of electrodes. In the example illustrated in FIGS. 1A-C electrode 32 is a hemispherical electrode and electrode 34 is a ring or coil electrode.

ICD 14 may deliver pacing pulses to heart 26 via a pacing or therapy vector that includes any combination of one or both of electrodes 32 and 34 and a housing or can electrode. For example, ICD 14 may deliver pacing pulses using a pacing or therapy vector between electrodes 32 and 34, deliver pacing pulses using a pacing or therapy vector between electrodes 32 and the conductive housing or can electrode of ICD 14, deliver pacing pulses using a pacing or therapy vector between electrodes 34 and the conductive housing 15 of ICD 14, or a combination thereof. In some instances, ICD 14 may deliver pacing therapy via a therapy vector between one of electrode 32 (or electrode 34) and defibrillation electrode 24. In still further instances, ICD 14 may deliver pacing therapy via a therapy vector between one of electrode 32 (or electrode 34) and one of sensing electrodes 28 or 30. ICD 14 may generate and deliver the pacing pulses to provide anti-tachycardia pacing (ATP), bradycardia pacing, post shock pacing, or other pacing therapies or combination of pacing therapies. In this manner, ATP therapy or post shock pacing (or other pacing therapy) may be provided in an IMD system 10 without entering the vasculature or the pericardial space, nor making intimate contact with the heart. Practice of the monomorphic VT therapy delivery techniques as disclosed herein, however, is not limited to the pacing lead arrangement shown and described here. A pacing lead and pacing electrodes are optional in a device configured to detect and treat VT according to the methods described below.

When pacing capability is present, ICD 14 may generate and deliver pacing pulses with any of a number of amplitudes and pulse widths to capture heart 26. The pacing thresholds of heart 26 when delivering pacing pulses substernally/retrosternally using pacing lead 18 may depend upon a number of factors, including location of electrodes 32 and 34, location of ICD 14, physical abnormalities of heart 26 (e.g., pericardial adhesions), or other factors. The pacing thresholds needed to capture heart 26 tend to increase with shorter pulse widths. In the case of ATP, ICD 14 may deliver pacing pulses having longer pulse widths than conventional ATP pulses delivered using intracardiac electrodes, for example, to reduce the amplitude of the pacing pulses.

ICD 14 may sense electrical activity of heart 26 via a combination of sensing vectors that include combinations of electrodes 32 and 34 and the housing or can electrode of ICD 14. For example, ICD 14 may obtain electrical signals sensed using a sensing vector between electrodes 32 and 34, obtain electrical signals sensed using a sensing vector between electrode 32 and the conductive housing or can electrode of ICD 14, obtain electrical signals sensed using a sensing vector between electrode 34 and the conductive housing or can electrode of ICD 14, or a combination thereof. In some instances, ICD 14 may sense electrical activity of heart 26 via a sensing vector between one of electrode 32 (or electrode 34) and electrodes 24, 28 and 30 of defibrillation lead 16. ICD 14 may deliver a pacing therapy as a function of the electrical signals sensed via the one or more of the sensing vectors of pacing lead 18. Alternatively or additionally, ICD 14 may deliver the pacing therapy as a function of the electrical signals sensed via the one or more of the sensing vectors of defibrillation lead 16.

ICD 14 also analyzes the sensed electrical signals from one or more of the sensing vectors of pacing lead 18 and/or one or more of the sensing vectors of defibrillation lead 16 or a combination thereof to detect tachycardia, such as VT or VF. In some instances, ICD 14 delivers one or more ATP therapies via the one or more pacing or therapy vectors of pacing lead 18 in response to detecting the tachycardia in an attempt to terminate the tachycardia without delivering a defibrillation shock. If the one or more ATP therapies are not successful or it is determined that ATP therapy is not desired, ICD 14 may deliver one or more cardioversion or defibrillation shocks via defibrillation electrode 24 of defibrillation lead 16. As will be described herein, the shock energy and the time the shock is delivered after detecting VT will be controlled based on discrimination between monomorphic VT and polymorphic VT performed by analyzing the morphology of QRS complexes or portions of the QRS complexes. In some cases, ATP therapy may be delivered prior to this analysis.

The configuration described above in FIGS. 1A-C is provides ventricular pacing via pacing lead 18. In situations in which atrial pacing is desired in addition to or instead of ventricular pacing, pacing lead 18 may be positioned further superior. A pacing lead configured to deliver pacing pulses to both the atria and ventricles may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. A pacing lead configured to deliver pacing pulses to only the atrium may, for example, have one or more electrodes located over a cardiac silhouette of the atrium as observed via fluoroscopy. In some instances, two substernal/retrosternal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy.

ICD 14 may include a housing 15 that forms a hermetic seal that protects components of ICD 14. The housing 15 of ICD 14 may be formed of a conductive material, such as titanium. ICD 14 may also include a connector assembly (also referred to as a connector block or header) that includes electrical feedthroughs through which electrical connections are made between conductors within leads 16 and 18 and electronic components included within the housing 15. As will be described in further detail herein, housing 15 may enclose one or more processors, memory devices, transmitters, receivers, sensors, sensing circuitry, therapy circuitry and other appropriate components. Housing 15 may function as a "can electrode" since the conductive housing or a portion thereof may be coupled to internal circuitry to be used as an indifferent or ground electrode during pacing or defibrillation shock delivery.

Leads 16 and 18 include a lead body that includes one or more electrodes located near the distal lead end or elsewhere along the length of the lead body. The lead bodies of leads 16 and 18 also contain one or more elongated electrical conductors (not illustrated) that extend through the lead body from the connector assembly of ICD 14 provided at a proximal lead end to one or more electrodes of leads 16 and 18. The lead bodies of leads 16 and 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may engage with respective ones of electrodes 24, 28, 30, 32, and 34. In one example, each of electrodes 24, 28, 30, 32, and 34 is electrically coupled to a respective conductor within its associated lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, 30, 32, and 34 and transmit sensed electrical signals from one or more of electrodes 24, 28, 30, 32, and 34 to the sensing module within ICD 14.

The examples illustrated in FIGS. 1A-C are illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this example, defibrillation lead 16 may be extend subcutaneously from the device toward the manubrium of the sternum and bend or turn and extend subcutaneously inferiorily from the manubrium of the sternum, substantially parallel with the sternum and pacing lead 18 may extend subcutaneously from the device toward the manubrium of the sternum to the desired location and bend or turn and extend substernally/retrosternally inferiorily from the manubrium of the sternum to the desired location.

In the example illustrated in FIG. 1A-C, system 10 is an ICD system that provides pacing therapy. However, these techniques may be applicable to other cardiac systems, including cardiac resynchronization therapy defibrillator (CRT-D) systems, cardioverter systems, or combinations thereof.

Numerous configurations may be contemplated that include one or more housing-based electrodes and/or one or more lead-based electrodes for enabling sensing of a subcutaneous ECG signal along one or more sensing vectors and for delivering electrical stimulation therapies to heart 26. IMD system 10 is referred to herein as a "extravascular IMD system" because leads 16 and 18 are positioned in an extravascular location outside the pericardium 38. It is understood that while ICD 14 and lead 18 may be positioned between the skin and a muscle layer of the patient 12, ICD 14 and any associated leads 16, 18 could be positioned in any extravascular location of the patient, such as below the muscle layer or even within the thoracic cavity.

The tachycardia discrimination and therapy delivery techniques disclosed herein are useful in an extravascular IMD system such as the system 10 shown in FIGS. 1A-C. A subcutaneous IMD system is less invasive and more easily implanted than a system including transvenous or epicardial leads. However, techniques disclosed herein may be implemented in other examples of IMD systems that include transvenous intracardiac leads and electrodes, epicardial electrodes or other lead and electrode systems. Examples of other IMD systems in which the techniques disclosed herein could be implemented are generally disclosed in U.S. Pat. No. 8,332,022 (Brown et al.) and U.S. Pat. No. 5,447,519 (Peterson), both of which patents are incorporated herein by reference in their entirety.

Further referring to FIG. 1A, a programmer 40 is shown in telemetric communication with ICD 14 by a communication link 42. Communication link 42 may be established between ICD 14 and programmer 40 using a radio frequency link such as Bluetooth, Wi-Fi, or Medical Implant Communication Service (MICS). Programmer 40 is used to retrieve data from ICD 14 and to program operating parameters and algorithms in ICD 14 for controlling ICD 14 functions. For example, programmer 40 may be used to program tachyarrhythmia detection parameters, such as VT and VF interval zones, VT and VF NID, and detection thresholds relating to morphology analysis of the ECG signals. Programmer 40 is also used to program therapy control parameters, such as the shock energy used to terminate VT or VF.

Figure 2:
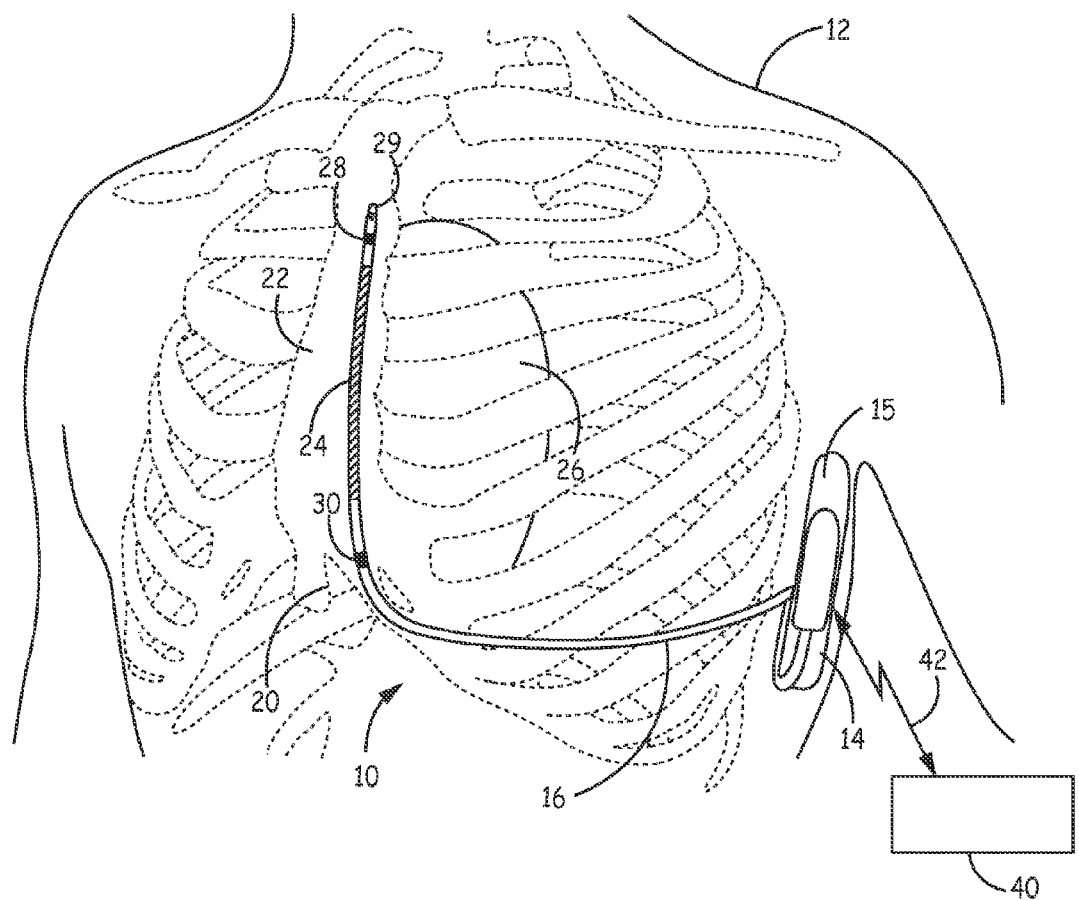
FIG. 2 is a conceptual diagram of a patient implanted with another example of an IMD system.

FIG. 2 is a conceptual diagram of patient 12 implanted with IMD system 10' including ICD 14 coupled to a single lead 16 carrying defibrillation electrode 24 and sensing electrodes 28 and 30. In this example, defibrillation shocks may be delivered using defibrillation electrode 24 and a housing or can electrode. Sensing and pacing of heart 26 may be performed using any combination of electrodes 24, 28, 30 and a housing or can electrode. ICD 14 and lead 16 are shown positioned in a similar manner as described above.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature.

Figure 3:
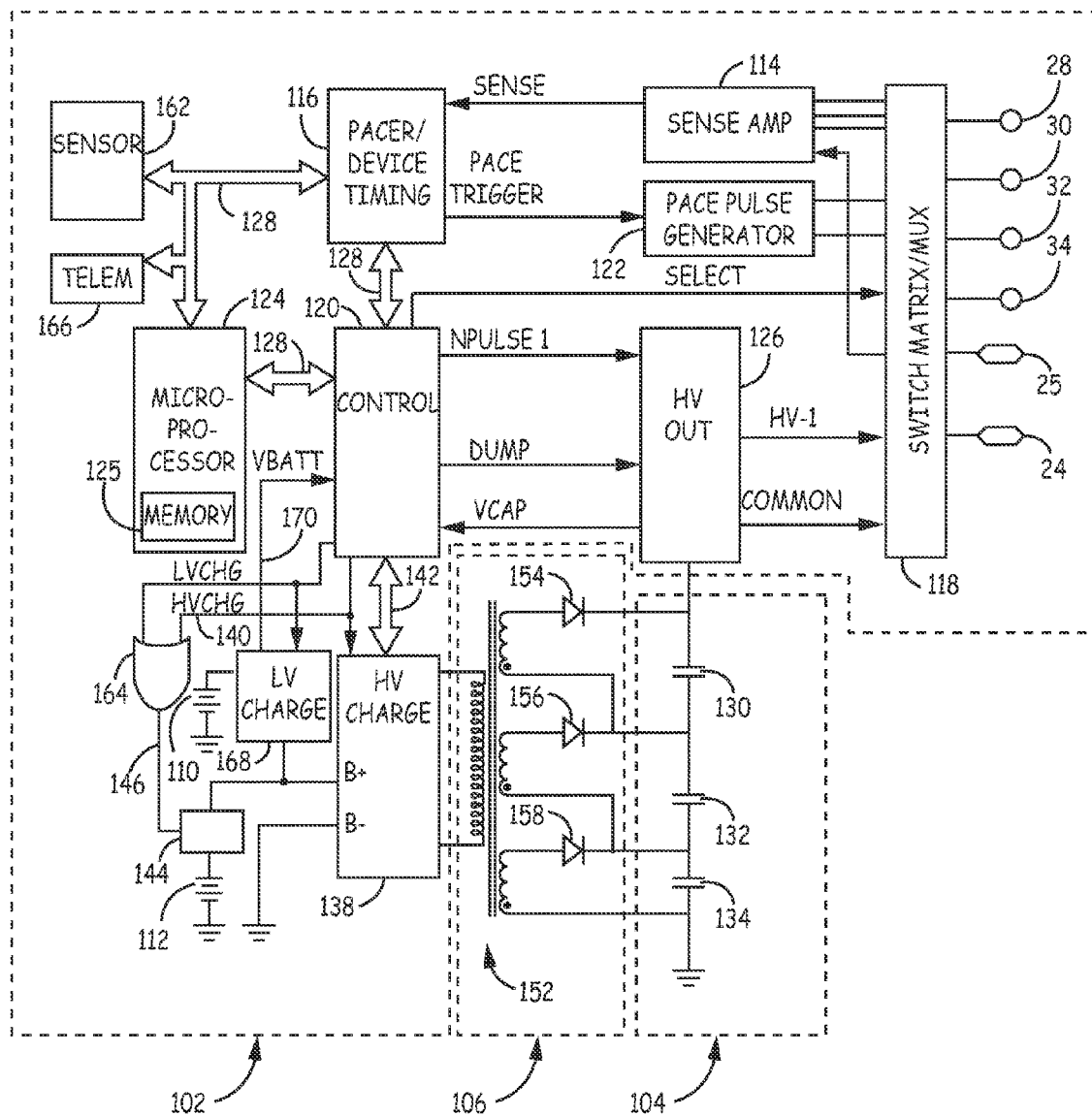
FIG. 3 is a functional block diagram of electronic circuitry included in the ICD included in the IMD system shown in FIG. 1 according to one example.

FIG. 3 is a schematic diagram 100 of ICD 14 according to one embodiment. The electronic circuitry enclosed within housing 15 includes software, firmware and hardware that cooperatively monitor the ECG, determine when a cardioversion-defibrillation shock or cardiac pacing is necessary, and deliver prescribed cardioversion-defibrillation and pacing therapies.

As illustrated in FIG. 3, ICD 14 includes one or more power sources such as a low voltage battery 110 and a high voltage battery 112. Low voltage battery 110 powers the ICD circuitry 102 and the pacing output capacitors (included in pace pulse generator 122) to supply cardiac pacing energy from pace pulse generator 122. The low voltage components, such as those associated with pacing, are charged to a preprogrammed voltage level by a low-voltage charging circuit 168 under control of the signal VBATT provided on signal line 170. Low voltage charging circuit 168 provides regulated power to the low voltage integrated circuits, hybrid circuits, and discrete components of the ICD circuitry 102. It is understood that although the system of FIG. 3 is shown to include both low voltage pacing therapy delivery capability and high voltage shock therapy delivery, the techniques disclosed herein may be employed in an IMD system that provides only high voltage cardioversion/defibrillation therapy.

In FIG. 3, sense amplifier 114 in conjunction with pacer/device timing circuit 116 processes the ECG signal that is developed across a particular ECG sense vector defined by a selected pair of the electrodes 28, 30 from lead 16 and/or electrodes 32, 34 if the second lead 18 is present as shown in FIG. 1A. The selection of a sensing electrode pair is made through the switch matrix/multiplexor (MUX) 118 in a manner to provide the most reliable sensing of an ECG signal of interest. Sense amplifier 114 may include two or more sensing channels for sensing and processing of multiple ECG signals sensed across different sensing vectors selected from electrodes 28, 30, 32, and 34, and in some embodiments electrode 24 and housing and/or can electrode 25, through switch matrix/MUX 118.

One or more ECG signals are passed through the switch matrix/MUX 118 to the input of the sense amplifier 114. Sense amplifier 114 passes R-wave sense signals to pacer/device timing circuit 116 when the ECG signal crosses an R-wave sensing threshold, which may be an auto-adjusting sensing threshold. Bradycardia or asystole is typically determined by a pacing escape interval timer expiring within the pacer timing circuit 116 and/or the control module 120 prior to receiving an R-wave sense signal. In response to the pacing escape interval expiring, a pace trigger signal is applied to the pace pulse generator 122 to generate a pacing pulse. The pacing escape interval is restarted upon a pacing pulse trigger or an R-wave sense signal. Bradycardia pacing is often provided temporarily to maintain cardiac output after delivery of a cardioversion-defibrillation shock that may cause the heart to slowly beat as it recovers back to normal function.

Initial detection of VT or VF is determined in the control module 120 and/or microprocessor 124, as a function of the intervals between R-wave sense event signals that are output from the pacer/device timing circuit 116 and sense amplifier circuit 114 to control module 120. Alternatively, some detection algorithms process time segments of the ECG morphology without sensing R-waves. Reference is made, for example, to U.S. Pat. No. 7,742,812 (Ghanem, et. al) and U.S. Pat. No. 8,160,684 (Ghanem, et. al), both of which patents are incorporated herein by reference in their entirety. Supplemental sensors, such as tissue color, tissue oxygenation, respiration, patient activity sensors or other physiological sensors may be used to contribute to the decision to apply or withhold a cardioversion/defibrillation therapy. Sensor processing unit 162 provides sensor signal data to microprocessor 124 via data bus 128.

Discrimination of monomorphic and polymorphic VT is performed by control module 120 and/or microprocessor 124 through analysis of the R-wave morphology of the sensed ECG signal(s) after an initial RR interval-based VT detection is made. The ECG signal is a far-field signal compared to an intracardiac electrogram (EGM) signal sensed using a bipolar pair of electrodes implanted within the heart. Beat to beat variation of the R-wave morphology during VT can be recognized through morphology analysis of the ECG signal. Sensing subcutaneous far field signals in the presence of noise may be aided by the use of appropriate denial and extensible accommodation periods as described in U.S. Pat. No. 6,236,882 (Lee, et al), hereby incorporated herein by reference in its entirety.

Certain steps in the performance of the detection algorithm described herein are cooperatively performed in microprocessor 124, including memory 125, associated circuitry, and stored detection criteria that may be programmed into memory 125 via a telemetry module 166. Data and commands are exchanged between microprocessor 124, control module 120, pacer/device timing circuit 116, and telemetry module 166 via a bi-directional data/control bus 128. The pacer/device timing circuit 116 and the control module 120 are clocked at a slow clock rate. The microprocessor 124 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection and discrimination procedures, and to update the time intervals monitored and controlled by the timers in pacer/device timing circuitry 116.

The algorithms and functions of the microprocessor 124 and control module 120 employed and performed in detection of VT and VF may include, for example, techniques disclosed in commonly assigned U.S. Pat. No. 5,354,316 (Keimel); U.S. Pat. No. 5,545,186 (Olson, et al.), and U.S. Pat. No. 5,855,593 (Olson, et al.), all of which patents are incorporated herein by reference in their entirety. Particular algorithms for detection of ventricular fibrillation and malignant ventricular tachycardias can include algorithms or techniques for distinguishing atrial and ventricular tachyarrhythmias from one another and from high rate sinus rhythms as generally set forth in the '316, '186, and '593 patents.

The detection algorithms are highly sensitive and specific for the presence or absence of life threatening VT and VF. ICD 14 includes a HV therapy delivery module including one or more HV output capacitors 130, 132, 134, collectively 104. When a malignant tachycardia is detected HV capacitors 104 are charged to a pre-programmed voltage level by a HV charging circuit 138. Charging of capacitors 104 is initiated when control module 120 issues a high voltage charge command HVCHG delivered on line 140 to high voltage charge circuit 138 and charging is controlled by means of bi-directional control/data bus 142 and a feedback signal VCAP from the HV output circuit 126. HV output capacitors 130, 132 and 134 may be of film, aluminum electrolytic or wet tantalum construction, for example.

The negative terminal of high voltage battery 112 is directly coupled to common ground (Vcc). A switch circuit 144 is normally open so that the positive terminal of high voltage battery 112 is disconnected from the positive power input of the high voltage charge circuit 138. Switch circuit 144 may be, for example, a field effect transistor (FET). The high voltage charge command HVCHG is conducted via conductor 146 to the control input of switch circuit 144, and switch circuit 144 closes in response to connect the positive terminal of high voltage battery to the positive power input B+ of high voltage charge circuit 138. HV charge circuit 138 is thereby rendered ready to begin charging the high voltage output capacitors 130, 132, and 134 with charging current from high voltage battery 112. In embodiments having both pacing and cardioversion/defibrillation, the ICD circuit 102 may be implemented with OR gate 164 to switch between a LVCHG signal and the HVCHG signal.

High voltage output capacitors 130, 132, and 134 may be charged to very high voltages, e.g., 700-3150V, to be discharged through the body and heart between coil electrode 24 and housing electrode 25. High voltage capacitors 130, 132 and 134 are charged by high voltage charge circuit 138 and a high frequency, high-voltage transformer 152. Proper charging polarities are maintained by diodes 154, 156 and 158 interconnecting the multiple secondary windings of high-voltage transformer 152 respectively associated with the capacitors 130, 132, and 134. The state of capacitor charge is monitored by circuitry within the high voltage output circuit 126 that provides a VCAP feedback signal indicative of the voltage to the control module 120. Control module 120 terminates the high voltage charge command signal HVCHG when the VCAP signal matches the programmed capacitor output voltage, i.e., the capacitor voltage required to deliver a programmed shock energy.

Control module 120 then develops control signal NPULSE 1 that is applied to the high voltage output circuit 126 for triggering the delivery of a cardioversion or defibrillation shocks. In particular, the NPULSE 1 signal triggers discharge of the capacitors 130, 132 and 134. In this way, control module 120 serves to control operation of the high voltage output circuit 126, which delivers high energy cardioversion/defibrillation shocks using coil electrode 24 coupled to the HV-1 output and housing electrode 25 coupled to COMMON output. A "therapy delivery module" as referred to herein includes, for example, HV output circuit 126, HV battery 112, HV charge circuit 138, capacitors 104, HV transformer circuit 106 and any other circuits or components used to deliver a HV shock therapy under the control of control module 120. If a normal cardiac rhythm returns before a shock is delivered, and a therapeutic shock is not required, control module 120 provides a DUMP control signal to high voltage output circuit 126, which causes the capacitors 104 to be discharged through a non-therapeutic load within ICD 14.

In the manner described above, control module 120 is configured to initiate charging of capacitors 104 to a voltage required to deliver a shock pulse at a programmed shock energy in response to detecting VT or VF. The programmed shock energy is typically the shock energy expected to be required to terminate a polymorphic VT (or VF) with a high degree of confidence and is generally greater than the shock energy required to terminate a monomorphic VT. The programmed shock energy may be at or near the maximum shock energy available from ICD 14. During capacitor charging, the ECG signal sensed using one or more sensing electrode vectors selected by switch matrix/MUX 118 from electrodes 28, 30, 32, 34 (and in some cases 24 and 25). The ECG signal is provided to microprocessor 124 by pacer/device timing circuit 116 for morphology analysis during capacitor charging. Pacer/device timing circuit 116 may include an analog-to-digital convertor for providing a digitized ECG signal to microprocessor 124. Microprocessor 124 analyzes the ECG signal(s) during charging of the capacitors 104 to determine if the ECG signal is monomorphic from beat-to-beat during the charging. Microprocessor 124 may therefore be programmed to perform a morphology analysis algorithm that compares the ECG signal during one heart beat or portion thereof occurring during capacitor charging to the ECG signal during another heart beat or portion thereof occurring during capacitor charging. Multiple beats are compared to each other to determine if the ECG signal appearance matches from one beat to the next indicating a monomorphic VT. Numerous morphology analysis techniques could be implemented for determining if beats occurring during capacitor charging are monomorphic. A wavelet transform method as disclosed in U.S. Pat. No. 6,393,316 (Gillberg et al.) is one example in which a morphology matching score is determined as a percentage, 100% indicating an exact match. Other methods may be used which compare the wave shape, amplitudes, slopes, inflection time points, number of peaks, or other features of the ECG signal, particularly of the R-wave or QRS complex.

If the ECG signal is determined to be a monomorphic VT signal during capacitor charging, the control module 120 is configured to terminate the capacitor charging and trigger an NPULSE1 signal applied to HV output circuit 126 prior to completing capacitor charging to the voltage required for delivering the programmed shock energy. HV output circuit 126 delivers an R-wave synchronized shock pulse at less than the programmed shock energy via coil electrode 24 and housing electrode 25. The shock pulse is delivered at the energy produced using the voltage accumulated on capacitors 104 at the time capacitor charging was terminated. In this way, a shock is delivered to quickly to terminate the monomorphic VT at a shock energy that is lower than the programmed shock energy but sufficient to terminate the monomorphic VT with a high probability.

Thus, ICD 14 monitors the patient's cardiac rhythm and initiates the charging for a cardioversion-defibrillation shock through the coil electrode 24 in response to detection of VT. The HVCHG signal causes the high voltage battery 112 to be connected through the switch circuit 144 with the high voltage charge circuit 138 and the charging of output capacitors 130, 132, and 134 to commence. Charging continues until the programmed charge voltage is reflected by the VCAP signal, or until the VT is determined to be monomorphic, whichever occurs earlier. At that point, control module 120 sets the HVCHG signal low terminating charging and opening switch circuit 144. Typically, the charging cycle takes less than fifteen to twenty seconds and will take much less when a monomorphic VT detection prematurely terminates capacitor charging. ICD 14 can be programmed to attempt to deliver cardioversion shocks to the heart in the manners described above in timed synchrony with a detected R-wave in conjunction with pacer/device timing circuit 116. ICD 14 may deliver defibrillation shocks to the heart without attempting to synchronize the delivery to an R-wave.

Episode data related to the detection of VT or VF and the delivery of a cardioversion or defibrillation shock may be stored in memory 125. Stored episode data is transmitted by telemetry module 166 to an external programmer 40 upon receipt of an interrogation command. Clinician review of episode data facilitates diagnosis and prognosis of the patient's cardiac state and therapy management decisions, including selecting programmable VT/VF detection and therapy delivery control parameters.

Circuitry and modules included diagram 100 shown in FIG. 3 represent functionality that may be included in an IMD of the present disclosure and may be implemented using any discrete and/or integrated electronic circuit components that include analog and/or digital circuits capable of producing the functions attributed to ICD 14 herein. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Memory 125 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Furthermore, memory 125 may include non-transitory computer readable storage media that stores executable instructions for causing ICD 14 to perform various functions described herein. The non-transitory computer readable media storing the instructions may include any of the media listed above, with the sole exception being a transitory propagating signal.

The functions attributed to ICD 14 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, VT detection operations performed by ICD 14 may be implemented in microprocessor 124 executing instructions stored in associated memory 125, control module 120, pacer/device timing 116, or any combination of microprocessor 124, control module 120 and pacer/device timing 116.

The telemetry communication module 166 includes an antenna and transceiver for performing bi-directional communication with programmer 40 as described above. Telemetry communication module 166 provides data received from programmer 40 to microprocessor 124 or control module 120 on data bus 128 and receives data for transmission to programmer 40 from microprocessor 124 and control module 120. Telemetry module 166 may include a dedicated communication control module, such as a microprocessor and associated memory, for performing communication algorithms that establish and maintain a communication link 42, decodes and encodes data, etc.

Figure 4:
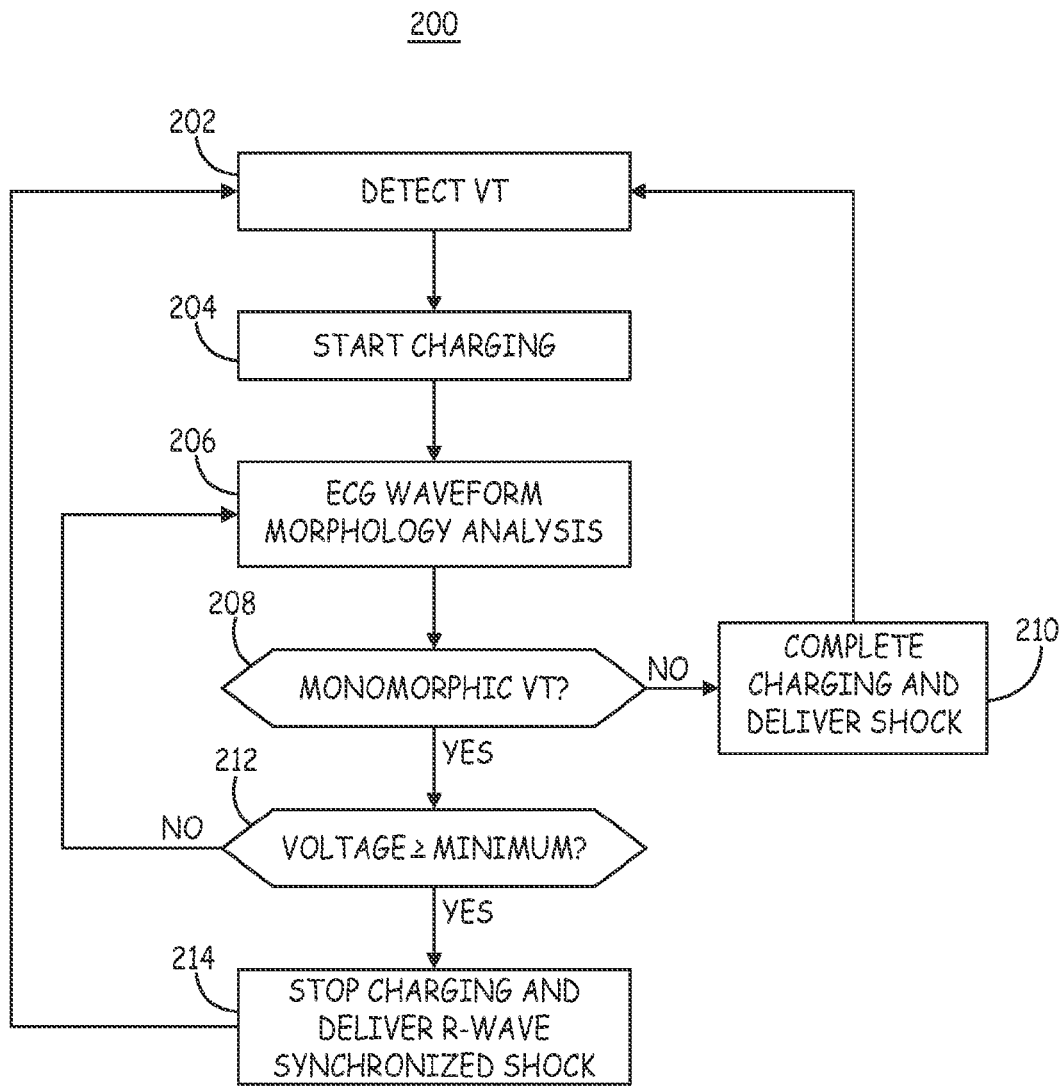
FIG. 4 is a flow chart of a method performed by the ICD for detecting a tachycardia and controlling therapy delivery.

FIG. 4 is a flow chart 200 of a method performed by ICD 14 for detecting monomorphic VT and controlling shock therapy delivery. At block 202, a VT is detected by ICD 14. The VT is detected from the sensed ECG signal(s) using a detection algorithm that may implement RR interval analysis, event pattern analysis, ECG morphology analysis, or any combination thereof.

Leading up to the VT detection at block 202, discrimination algorithms may be performed to confirm that a detected tachycardia is VT and not supraventricular tachycardia (SVT). SVT is generally considered a non-shockable rhythm so that a shock therapy is withheld when SVT is detected. The algorithm shown by flow chart 200 is used when the detected rhythm is determined to be a shockable rhythm, i.e. VT or VF. The VT may or may not be determined to be monomorphic or polymorphic at the time of detection at block 202. Examples of detection and discrimination algorithms that may be used to detect VT are generally disclosed in the above-incorporated '812 and '684 patents and in commonly-assigned U.S. Pat. No. 6,393,316 (Gillberg et al.) and U.S. Pat. No. 8,401, 629 (Stadler, et al.) incorporated herein by reference in its entirety.

In response to detecting VT, the IMD control module 120 initiates charging of the HV output capacitors 104 by HV charging circuit 138 at block 204. The HV charging circuit 138 is controlled to initiate charging to a voltage required to deliver a programmed shock energy for treating polymorphic VT or VF. This programmed energy may be at or near a maximum shock energy available, particularly if subcutaneous defibrillation electrodes are being used, in order to terminate a polymorphic VT or VF on the first shock attempt with a high probability. The programmed shock energy may be greater than the shock energy needed to terminate a monomorphic VT but would be required if the VT is a more serious polymorphic VT or VF.

Accordingly, during charging of the capacitors 104, the microprocessor 128 analyzes the ECG signal morphology to determine if the detected VT is monomorphic at block 206. If the detected VT is determined to be monomorphic during capacitor charging (block 208), the control module 120 triggers HV output circuit 126 to deliver the accumulated charge on capacitors 104 prematurely. "Premature" delivery of the accumulated charge is the delivery of a cardioversion shock when the capacitors 104 are partially charged, i.e. prior to being completely charged to the voltage required to deliver the programmed shock energy. In one example, as soon as the VT is determined to be monomorphic during capacitor charging, based on a morphology analysis algorithm performed during charging, the capacitor charging is terminated and an R-wave synchronized shock is delivered using the available capacitor voltage at block 214.

In some examples, a shock is delivered at less than the full programmed shock energy only if the heart rate is less than a predetermined threshold. As such, an additional criterion may be applied at block 208 which requires the VT to be monomorphic and a predetermined number of most recent R-R intervals are greater than a threshold interval. For example, the R-wave synchronized shock may be delivered if the VT is monomorphic and the most recent eight R-R intervals are greater than a default or programmed minimum interval.

In other embodiments, the control module 120 may verify that a minimum capacitor voltage has been reached for delivering a minimal acceptable shock energy. For example, upon determining (at block 208) that the detected VT is monomorphic after starting capacitor charging, the control module 120 may compare the current voltage of capacitors 104 (VCAP signal) to a predetermined minimum voltage value that is less than the voltage required for delivering the full programmed shock energy. For example, the VCAP feedback signal may be compared to a minimum voltage desired for delivering a shock pulse. This minimum voltage required for delivering a monomorphic VT shock may result in a shock energy that is less than a defibrillation threshold measured in the patient during device testing. To illustrate, a full programmed shock energy for treating polymorphic VT or VF may be 15 Joules or more, e.g. at least 25 Joules, and a minimum monomorphic VT shock energy may be 5 Joules or less, e.g. as low as 1 Joule.

In order to determine if a minimum required voltage has been reached, the capacitor voltage may be measured and used to estimate a deliverable shock energy. The estimated deliverable shock energy may then be compared to a programmed or default minimum shock energy. If the estimated shock energy is less than the minimum shock energy, the minimum required voltage has not yet been reached.

If the capacitor voltage has not reached a required minimum as determined at block 212, the ECG morphology analysis continues during the ongoing capacitor charging process. If the capacitor voltage reaches at least the predetermined minimum voltage, as determined at block 212, the control module 120 terminates charging of capacitors 104 at block 214 and triggers the HV output circuit 126 to deliver an R-wave synchronized shock, prior to completing charging of the capacitors to a voltage required for delivering the full, programmed shock energy. The shock is delivered at block 214 using the present voltage on the capacitors 104. The process may return to block 202 after delivering the shock at less than the programmed shock energy to determine if VT is still being detected at block 202. If VT is redetected, the full programmed shock energy may be delivered. Alternatively, the process shown by flow chart 200 may be repeated, but the minimum required capacitor voltage for delivering a monomorphic VT shock therapy may be increased.

The minimum acceptable shock energy for treating monomorphic VT may be programmable by a clinician or may be a fixed nominal value. When the minimum shock energy is programmable, the clinician or other user will program the full shock energy for treating unspecified VT (including polymorphic VT) with a high likelihood of success and program the minimum shock energy acceptable for treating monomorphic VT when capacitor charging is terminated prematurely. Whenever capacitor charging begins in response to VT detection, charging to the full programmed shock energy is initiated. That charging process is terminated early if the VT is determined to be monomorphic during charging and the capacitor voltage required to deliver the programmed minimum shock energy has been reached. As used herein, the "programmed shock energy" refers to the relatively higher shock energy programmed for treating polymorphic VT or VF unless otherwise specified. The term "minimum shock energy," which may be a programmable value, refers to the relatively lower shock energy that is acceptable for treating monomorphic VT.

If the detected VT is not determined to be monomorphic at block 208, at any time during charging, the capacitor charging is completed to deliver the full, programmed shock energy at block 210. In this way, even if the VT was initially determined to be monomorphic at block 202 and/or at block 208 during charging, but advanced to a polymorphic VT before the capacitor charging reached the minimum voltage for delivering a monomorphic VT shock therapy, the charging process is completed and the full, programmed shock energy is delivered.

In some embodiments, the control module 120 may deliver a shock as soon as the two conditions of monomorphic VT detection is made after charging has started and a minimum capacitor voltage is reached. If one or the other of these two conditions is not reached, capacitor charging continues until both conditions are satisfied or until the capacitors are fully charged according to the programmed full shock energy.

In other examples, if a polymorphic VT is detected upon initial VT detection or during charging, no further morphology analysis for discriminating monomorphic VT and polymorphic VT is performed. Capacitors 104 are fully charged to deliver the full, programmed shock energy. It is assumed that once the VT has advanced to a polymorphic from of VT, it will not improve to a more regular, monomorphic form of VT.

Figure 5:
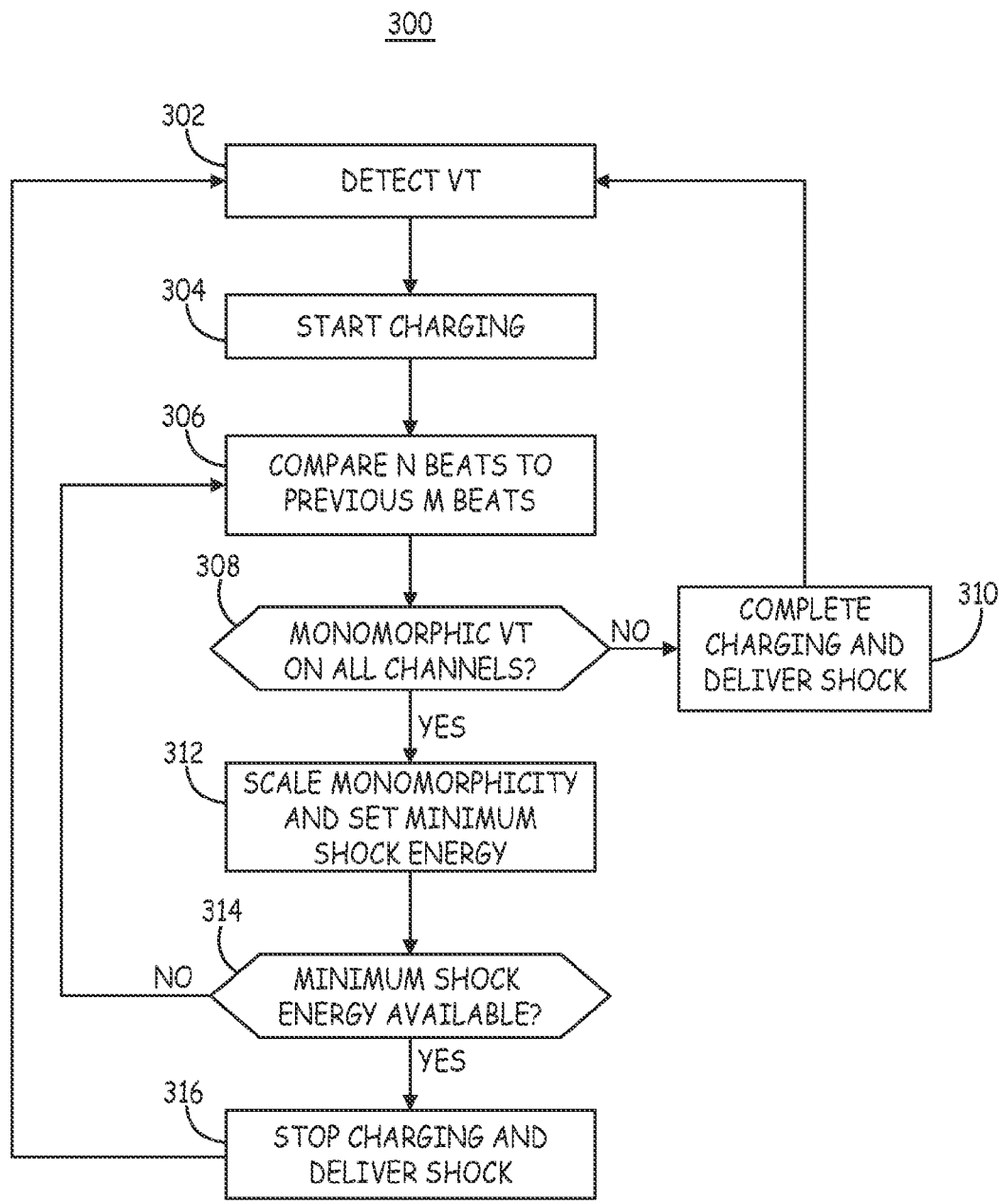
FIG. 5 is a flow chart of a method for controlling shock therapy according to another example.

FIG. 5 is a flow chart 300 of a method for controlling shock therapy according to another example. At block 302, VT is detected according to an implemented detection algorithm. At block 304, capacitor charging is initiated in response to detecting the shockable VT rhythm. During charging, morphology analysis is performed to determine if the VT is monomorphic at a time when the capacitors are partially charged to a voltage corresponding to a programmed shock energy. Accordingly, the ECG signal, in particular the R-wave or QRS complex or portion thereof, in a set of a predetermined number of beats is compared to a previous set of a predetermined number of beats to determine if the sets of beats match each other. Polymorphic and multimorphic VT often have adjacent beat morphologies that are the same or similar. Comparing one R-wave to a previous R-wave may not be sufficient to reliably distinguish monomorphic and polymorphic VT. A set of at least two or more consecutive R-waves is compared to a previous set of two or more R-waves to detect monomorphic VT in some examples. Multiple sets may be compared.

For example, the morphology for the current N beats may be compared to the previous M beats. N and M may be equal or unequal. To illustrate, a morphology matching score may be determined between a current beat and each of the previous five beats. The morphology comparisons are between beats sensed during charging and beats sensed before and/or during charging to determine if the VT is monomorphic. No template is required to discriminate between monomorphic and polymorphic VT because the beats (i.e. R-waves) are compared to each other. A matching score or index is determined from the morphology comparisons between sets of beats occurring during the current VT episode without generating and storing a QRS or R-wave template from another cardiac rhythm prior to VT detection.

In comparing a set of beats to another set of beats, wherein each set includes more than one R-wave, each R-wave in the first set may be compared to each R-wave in the second set. Alternatively, the first R-waves in each set may be compared to each other; the second R-waves in each set may be compared to each other, and so on. In yet another example, an n-second ECG signal segment comprising two or more R-waves may be compared to a preceding n-second ECG signal segment to obtain a morphology matching score. The morphology matching score may be compared to a monomorphic VT detection threshold.

The morphology analysis may be performed using one or more ECG signals when multiple sensing channels are available for sensing a far field signal. For example, switch matrix 118 may couple two different pairs of electrodes selected from electrodes 28 and sense electrode 26 to sense amplifier 114. Pacer/device timing circuit 116 provides two ECG signals to microprocessor 124 for morphology analysis. If both ECG signals are determined to be monomorphic from beat to beat, a positive monomorphic VT detection is made at block 308. If one signal (or channel) is determined to present a polymorphic VT, the rhythm is detected as polymorphic VT and the process advances to block 310. Capacitor charging required to deliver the full, programmed shock energy is completed and the shock is delivered at the programmed energy for treating polymorphic VT or VF.

During the comparison process at block 306, the R-wave signals are not normalized such that a VT rhythm having changes in R-wave amplitude but no change in wave shape can be discriminated from truly monomorphic rhythms. If the R-wave amplitude changes, e.g. a waxing and waning of amplitude, the rhythm is detected as a polymorphic VT. This type of amplitude-modulated VT is not treated as a monomorphic rhythm even if the normalized R-wave morphology is highly regular. In other examples, R-wave signals may be normalized such that wave shape is compared without examining differences in amplitude.

In the method described above in conjunction with FIG. 4, if a VT is determined to be monomorphic, charging is terminated before the capacitor voltage reaches the full programmed shock energy level and the R-wave synchronized shock is delivered. In the example of FIG. 5, if the VT is detected as being monomorphic, the monomorphicity of the ECG signal may be scaled to enable a minimum shock energy to be determined based on the degree of regularity of the VT morphology before the shock is delivered.

In some examples, the monomorphicity is scaled at block 312. As used herein, "monomorphicity" refers to the degree of morphology regularity of R-waves during a detected VT. This morphology regularity refers to wave shape and amplitude and does not refer to R-R intervals in this case. This degree of regularity is determined by a morphology matching score or other index or measure used to quantify how well the R-wave morphology matches between sets of consecutive R-waves. To illustrate, a high monomorphicity may be indicated by a morphology matching score of 95% or greater between sets of consecutive beats. A moderate monomorphicity may be a morphology matching score of 90% or greater for the sets of consecutive beats. A low monomorphicity may be a morphology matching score greater than 85% for the sets of consecutive beats. Any scores lower than 85% may result in a polymorphic VT detection and delivery of the full programmed shock energy. In this example, three different ranges of monomorphicity are defined based on percentage matching scores that may be determined using a wavelet transform analysis. In other examples, two or more levels of monomorphicity may be defined using a morphology matching score and/or other criteria. For example, the amount of amplitude modulation and the variation in wave shape may both be quantified and used to determine a scaled monomorphicity. In some embodiments, scaling the monomorphicity includes determining a variation in R-wave amplitude when the amplitude-normalized R-wave morphology is monomorphic and/or determining a variation in wave shape using non-normalized R-waves.

The minimum acceptable energy for delivering a shock for treating the monomorphic rhythm is scaled to the monomorphicity of the detected VT. Based on a scaled monomorphicity determined at block 306, the minimum voltage level for the capacitors is set at block 312. Different minimum shock energy levels may be programmed by a clinician for different monomorphicities. When the scaled monomorphicity is determined, the capacitor voltage is compared to a voltage required to deliver a minimum shock energy programmed for the determined monomorphicity.

If the monomorphicity is high, a relatively lower shock energy may be successful in terminating the VT than if the monomorphicity is moderate or low. The minimum voltage may be scaled as a percentage of the voltage required to deliver the full programmed shock energy for treating polymorphic VT or VF. For example, if the monomorphicity is high, the minimum may be set at 10% of the full programmed shock energy for treating polymorphic VT. If the monomorphicity is moderate, the minimum may be set at 30% of the full programmed shock energy, and if the monomorphicity is low, the minimum may be set at 50% of the full programmed shock energy. These percentages are examples and different levels of the required minimum shock energy for treating different degrees of monomorphicity may be programmable by a clinician in Joules or as a percentage of the full programmed shock energy for treating polymorphic VT or VF.

After setting the minimum shock energy according to the scaled monomorphicity of the detected VT, the voltage of the capacitors currently reached during charging is used to estimate a deliverable shock energy that is compared to the scaled minimum shock energy at block 314. If the actual capacitor voltage is high enough to deliver an estimated shock energy equal to or greater than the scaled minimum shock energy, the charging is terminated at block 316. A shock is delivered, synchronized to a subsequent R-wave, using the partially charged capacitor voltage. Capacitor charging may be terminated as soon as the capacitor voltage has been determined to be at or greater than a minimum voltage required or it may continue during R-wave sensing performed for the synchronization of the shock such that additional capacitor charging is achieved right up to the time of shock delivery. The process returns to block 302 after shock delivery.

If a monomorphic VT is still being detected at block 302 after delivering a first shock but the monomorphicity is decreased, the minimum shock energy on a subsequent shock is scaled upward accordingly. Alternatively, if a shock therapy less than the full programmed shock energy for treating polymorphic VT or VF is delivered once in response to monomorphic VT detection but VT is still being detected, the next shock attempt may be delivered at the full programmed shock energy independent of whether the VT is still monomorphic or not.

Figure 6:
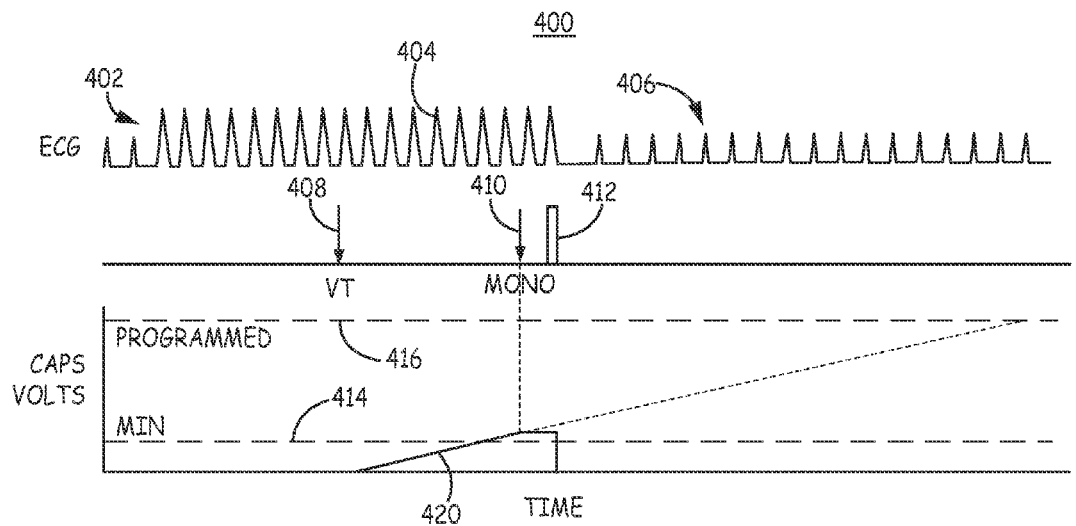
FIG. 6 is a timing diagram depicting operations performed by the ICD in discriminating and treating monomorphic VT.

FIG. 6 is a timing diagram 400 depicting operations performed by ICD 14. An ECG signal 402 is sensed by ICD 14 for detecting monomorphic VT 404. A VT detection is made at 408, for example in response to detecting a required number of VT intervals as determined from the ECG signal 402. Upon VT detection 408, capacitor charging 420 begins. During capacitor charging 420, the ECG 402 is analyzed to determine if the R-wave morphology from a set of beats sensed during charging 420 matches a preceding set of beats. If a required number of R-waves match, the VT is detected as monomorphic at 410. Capacitor charging 420 is immediately terminated, and a shock 412 is delivered synchronized to the next R-wave using the available capacitor charge. In other examples, capacitor charging 420 may continue after the monomorphic detection is made at 410 up until delivery of shock 412 in order to gain additional charging time during the R-wave synchronization process and thereby increase the capacitor voltage even further for delivering shock 412.

As described previously, in some embodiments the capacitor voltage is compared to a minimum required capacitor voltage 414 for delivering a minimum shock energy. If the minimum voltage 414 has not been reached upon detecting the monomorphic VT at 410, charging 420 continues until both conditions of the minimum capacitor voltage 414 and detection of monomorphic VT are satisfied. If the VT is no longer monomorphic by the time the capacitor voltage reaches the required minimum 414, the capacitor(s) are completely charged to the voltage 416 required for delivering the full programmed shock energy for treating polymorphic VT or VF.

As can be seen in FIG. 6, the charge time required to reach the programmed voltage 416 is considerably longer than the charge time required to reach the minimum voltage 414. When monomorphic VT is detected, therefore, early treatment by relatively lower energy shock pulse 412 can restore sinus rhythm 406 precluding a worsening of the monomorphic VT to a polymorphic VT or VF. IMD battery energy is conserved and the patient's exposure to high energy shocks is reduced.

As described in conjunction with FIG. 5, the minimum voltage 414 may be scaled to a determined monomorphicity of the ECG signal 402. The actual capacitor voltage may be compared to different minimum voltage values during charging 420 depending on the scaled monomorphicity. If shock 412 fails to terminate the monomorphic VT, the minimum voltage 414 may be increased for future monomorphic VT detections to improve the likelihood of terminating monomorphic VT using an early shock pulse having a lower energy than the full programmed shock energy used for treating polymorphic VT or VF. In this way, the minimum capacitor voltage 414 may be "learned" or automatically adjusted over time based on the success or failure of the early shock pulse 412 and the corresponding monomorphicity of the R-waves 404 occurring during charging 420.

Figure 7:
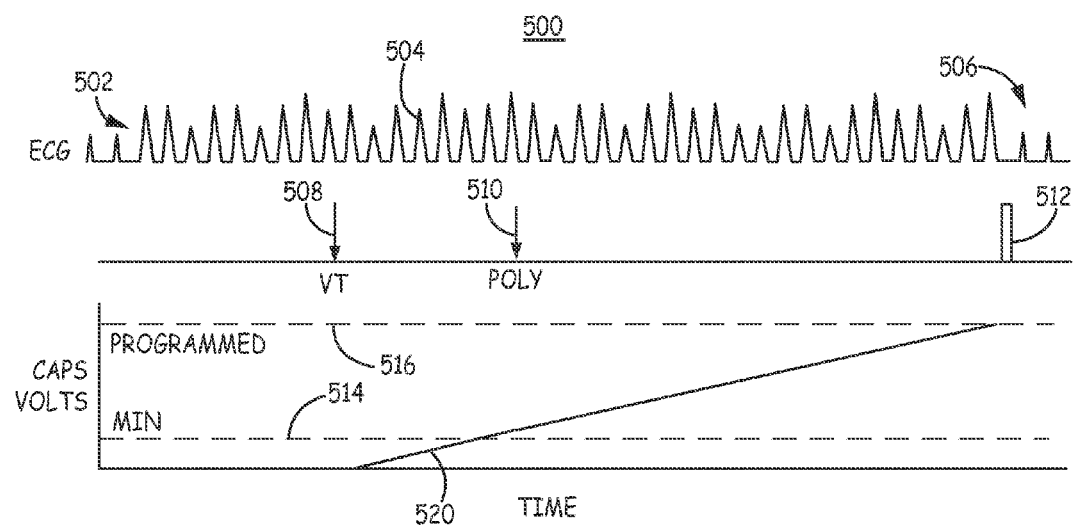
FIG. 7 is a timing diagram depicting operations performed by the ICD when a detected VT is polymorphic.

FIG. 7 is a timing diagram 500 depicting operations performed by ICD 14 when a detected VT is polymorphic. The ECG signal 502 is sensed by ICD 14 for detecting VT signals 504. A VT detection is made at 508, for example in response to detecting a required number of VT intervals as determined from the ECG signal 502. Upon VT detection 508, capacitor charging 520 begins. During capacitor charging 520, the ECG 502 is analyzed to determine if the R-wave morphology from a set of beats sensed during charging 520 matches a preceding set of beats. Two or more sets of beats may be compared with each beat set including two or more beats. If a morphology matching criterion for detecting monomorphic VT is not satisfied as a result of the comparison, the VT is detected as polymorphic at 510. Capacitor charging 520 continues until the capacitor voltage meets the programmed shock energy voltage 516 for treating a polymorphic VT or VF. A shock 512 is delivered at the programmed shock energy to restore sinus rhythm 506. The shock 512 may or may not be synchronized to an R-wave.

Figure 8:
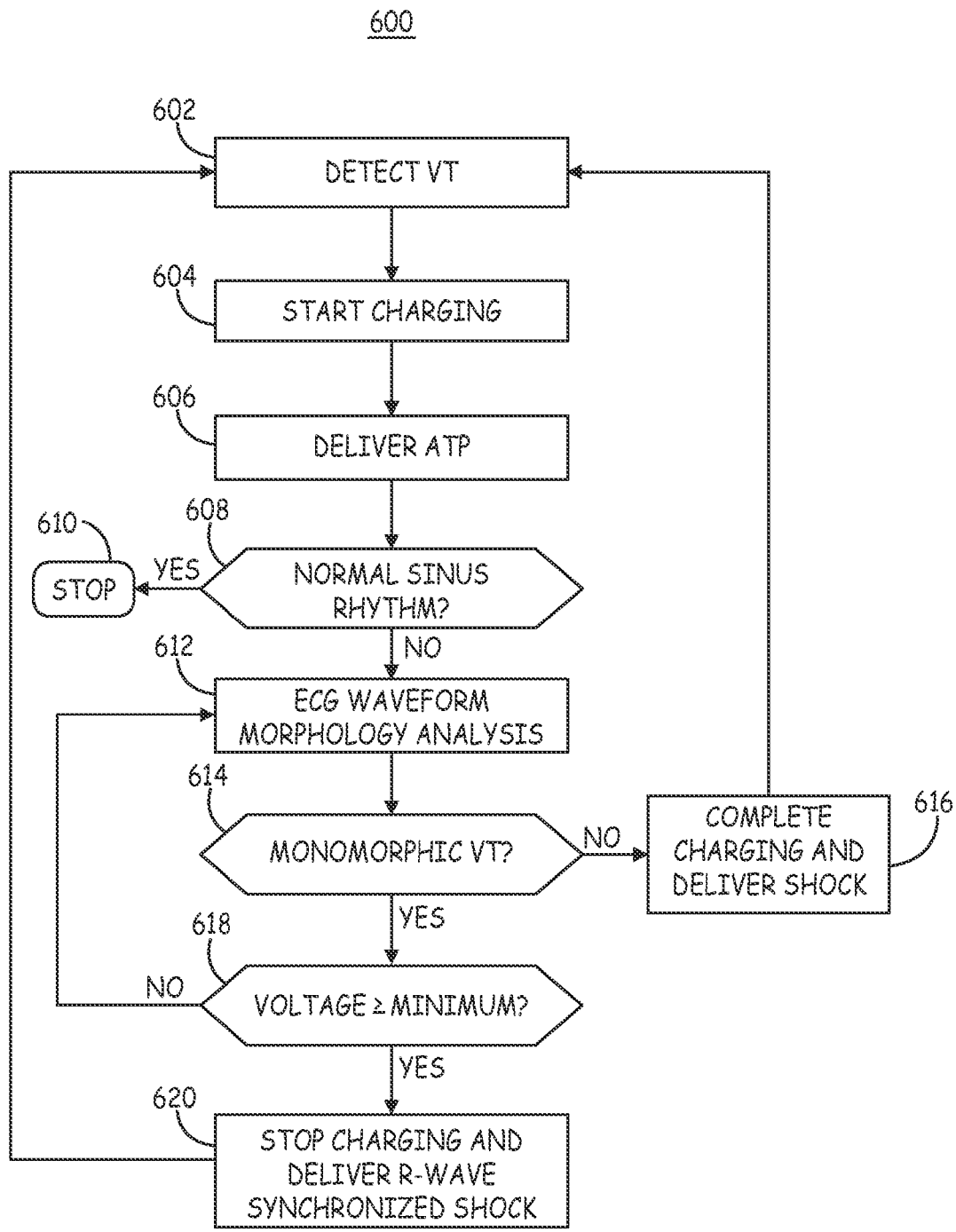
FIG. 8 is a flow chart a therapy delivery method including anti-tachycardia pacing (ATP) for treating a detected VT.

FIG. 8 is a flow chart 600 of a therapy delivery method for treating a detected VT including anti-tachycardia pacing (ATP). At block 602, VT is detected and capacitor charging to the full programmed shock energy for treating polymorphic VT or VF is initiated at block 604. During charging, ATP is delivered at block 606 as an initial attempt to terminate the VT using a low voltage therapy. Techniques for delivering ATP during capacitor charging are generally disclosed in commonly-assigned U.S. Pat. No. 8,170,663 (DeGroot, et al.), hereby incorporated herein by reference in its entirety. If normal sinus rhythm is restored, as determined at block 608, no further therapy is required and the process is terminated at block 610.

If normal sinus rhythm is not restored by ATP, morphology analysis is performed at block 612 to determine if the detected VT is monomorphic. When ATP is delivered during charging, the morphology analysis to discriminate monomorphic VT is performed after ATP has been delivered. ECG signal morphology recorded prior to or during ATP is not used since the ATP may alter the arrhythmia. As described previously, at least one ECG signal segment or portion thereof including at least two R-waves matches is compared to at least one previous ECG signal segment or portion thereof including at least two R-waves. If the comparison of at least two ECG signal segments results in a match according to monomorphic VT detection criteria, e.g. greater than a 90% morphology matching score, the capacitor voltage is used to estimate a deliverable shock energy which is compared to a minimum shock energy at block 618. When the minimum shock energy can be delivered, charging is terminated and an R-wave synchronized shock is delivered at block 620. If the VT is not monomorphic after delivering ATP, capacitor charging is completed to deliver the full programmed shock energy for treating a polymorphic VT or VF at block 616.

When the feature of ATP during charging is enabled but fails to terminate a detected VT, subsequent VT detections may or may not trigger ATP during capacitor charging. Morphological analysis may begin immediately upon initiating charging to allow a monomorphic VT to be detected and treated early by a shock energy less than the full shock energy programmed for treating polymorphic VT.

Thus, a method and apparatus for detecting and treating monomorphic VT have been presented in the foregoing description with reference to specific embodiments. In other examples, various methods described herein may include steps performed in a different order or combination than the illustrative examples shown and described herein as long as the decision to deliver a shock pulse at an energy that is less than a programmed full shock energy is made after initiating capacitor charging and in response to morphology analysis performed during the capacitor charging. It is appreciated that various modifications to the referenced embodiments may be made without departing from the scope of the disclosure as set forth in the following claims.

The invention claimed is:

1. A method performed by a medical device, comprising:
    sensing a cardiac signal using a plurality of electrodes coupled to a sensing module of the medical device;
    detecting a ventricular tachycardia in response to the cardiac signal;
    initiating, by a control module, charging of a capacitor to deliver a programmed shock energy for treating a polymorphic ventricular tachycardia in response to detecting the ventricular tachycardia;

determining by a processor if the ventricular tachycardia during the charging is monomorphic;

responsive to the ventricular tachycardia being monomorphic during the charging, terminating the charging of the capacitor; and delivering a shock pulse at less than the programmed shock energy.

2. The method of claim 1, further comprising:

storing a value corresponding to a minimum shock energy;

measuring a capacitor voltage in response to the ventricular tachycardia being monomorphic during the charging;

estimating an available shock energy using the measured capacitor voltage;

comparing the estimated shock energy to the minimum shock energy; and continuing charging the capacitor before delivering the shock pulse at less than the programmed shock energy if the estimated available shock energy is less than the minimum shock energy.

3. The method of claim 1, further comprising:

simultaneously monitoring a voltage on the capacitor and a morphology of the detected tachycardia during the charging; and delivering the shock pulse in response to both the voltage reaching at least a predetermined minimum and the ventricular tachycardia being monomorphic.

4. The method of claim 1, wherein determining if the ventricular tachycardia is monomorphic comprises comparing a first set of at least two cardiac signal waveforms to a second set of at least two cardiac signal waveforms to determine a morphology matching score without comparing the cardiac signal to a template determined before detecting the ventricular tachycardia.

5. The method of claim 1, further comprising:

scaling a monomorphicity of the detected ventricular tachycardia if the ventricular tachycardia is determined to be monomorphic during the charging;

setting a minimum shock energy less than the programmed shock energy in response to the scaled monomorphicity; and delivering the shock pulse when the capacitor reaches a required voltage for delivering the minimum shock energy.

6. The method of claim 5, wherein scaling the monomorphicity comprises determining a morphology matching score by comparing at least two waveforms of the cardiac signal occurring during the charging to a preceding at least two waveforms of the cardiac signal and comparing the morphology matching score to a plurality of scaling ranges.

7. The method of claim 5, wherein scaling the monomorphicity comprises determining a variation in R-wave amplitude when a normalized R-wave morphology is monomorphic.

8. The method of claim 1, wherein determining if the detected tachycardia is monomorphic comprises comparing a first non-normalized R-wave of the cardiac signal occurring during the charging to a second non-normalized R-wave of the cardiac signal occurring during the charging.

9. The method of claim 1, further comprising:

wherein sensing the cardiac signal comprises sensing a first cardiac signal on a first channel and a second cardiac signal on a second channel;

determining if the first cardiac signal is monomorphic during the charging;

determining if the second cardiac signal is monomorphic during the charging; and completing the charging of the capacitor and delivering a shock pulse at the programmed shock energy if one of the first cardiac signal and the second cardiac signal is not monomorphic during the charging.

10. The method of claim 1, further comprising delivering anti-tachycardia pacing during the charging and before determining if the ventricular tachycardia during the charging is monomorphic.

11. A medical device, comprising:

a plurality of electrodes for acquiring a cardiac signal;

a sensing module coupled to the plurality of electrodes for sensing the cardiac signal;

a therapy delivery circuit coupled to the plurality of electrodes for delivering a shock pulse;

a control module configured to initiate charging of a capacitor to a voltage required to deliver the shock pulse at a programmed shock energy in response to detecting the ventricular tachycardia; and a processor configured to determine if the ventricular tachycardia is monomorphic during the charging, the control module configured:

terminate the charging of the capacitor in response to the ventricular tachycardia being monomorphic during the charging, and control the therapy delivery circuit to deliver a shock pulse at less than the programmed shock energy.

12. The device of claim 11, further comprising:

a memory for storing a value corresponding to a minimum shock energy;

the control module further configured to:

measure a voltage of the capacitor in response to the ventricular tachycardia being monomorphic during the charging;

estimate an available shock energy using the measured capacitor voltage;

compare the estimated shock energy to the minimum shock energy; and continue charging the capacitor before delivering the shock pulse at less than the programmed shock energy if the estimated available shock energy is less than the minimum shock energy.

13. The device of claim 11, wherein the control module is further configured to:

simultaneously monitor a voltage on the capacitor and a morphology of the cardiac signal during the charging; and control the therapy delivery circuit to deliver the shock pulse at less than the programmed shock energy in response to both the voltage reaching a predetermined minimum and the ventricular tachycardia being monomorphic.

14. The device of claim 11, wherein determining if the cardiac signal is monomorphic during the charging comprises comparing a first set of at least two cardiac signal waveforms to a second set of at least two cardiac signal waveforms to determine a morphology matching score without comparing to a template that is determined before detecting the ventricular tachycardia.

15. The device of claim 11, wherein the processor and the control module are configured to cooperatively:

scale a monomorphicity of the detected tachycardia if the tachycardia is determined to be monomorphic;

set a minimum shock energy less than the programmed shock energy in response to the scaled monomorphicity; and deliver the shock pulse when the capacitor reaches a required voltage for delivering the minimum shock energy.

16. The device of claim 15, wherein scaling the monomorphicity comprises determining a morphology matching score by comparing at least two waveforms of the cardiac signal occurring during the charging to a preceding at least two waveforms and comparing the morphology matching score to a plurality of scaling ranges.

17. The device of claim 15, wherein scaling the monomorphicity comprises determining a variation in R-wave amplitude of the cardiac signal occurring during the charging when a normalized R-wave morphology is monomorphic.

18. The device of claim 11, wherein determining if the cardiac signal is monomorphic comprises comparing a first non-normalized R-wave of the cardiac signal occurring during the charging to a second non-normalized R-wave of the cardiac signal occurring during the charging.

19. The device of claim 11, further comprising:
the sensing module comprising a first channel for sensing a first cardiac signal using a first pair of the plurality of electrodes and second channel for sensing a second cardiac signal using a second pair of the plurality of electrodes;
the processor configured to:
determine if the first cardiac signal is monomorphic during the charging;
determine if the second cardiac signal is monomorphic during the charging; and
the control module configured to complete the charging of the capacitor and control the therapy delivery circuit to deliver the shock pulse at the programmed shock energy if one of the first cardiac signal and the second cardiac signal is not monomorphic during the charging.

20. The device of claim 11, wherein the control module is further configured to control the therapy delivery module to deliver anti-tachycardia pacing during the charging and before determining if the ventricular tachycardia during the charging is monomorphic.

21. The device of claim 11, wherein the control module is configured to control the therapy delivery circuit to deliver the shock pulse by delivering an accumulated charge of the capacitor when the charging is terminated, the accumulated charge being less than the voltage required to deliver the programmed shock energy.

22. A non-transitory, computer-readable medium storing a set of instructions, which cause a medical device to perform a method comprising:

sensing a cardiac signal using a plurality of electrodes coupled to a sensing module of the medical device;
detecting a ventricular tachycardia in response to the cardiac signal;
initiating, by a control module, charging of a capacitor to a voltage required to deliver a programmed shock energy in response to detecting the ventricular tachycardia;
during the charging, determining by a processor if the cardiac signal is monomorphic ventricular tachycardia during the charging;
responsive to the cardiac signal being monomorphic ventricular tachycardia during the charging, terminating the charging of the capacitor; and
delivering a shock pulse at less than the programmed shock energy.

23. A medical device, comprising:
means for sensing a cardiac signal;
means for detecting a ventricular tachycardia in response to the cardiac signal;
control means for initiating charging of a capacitor to a voltage required to deliver a programmed shock energy in response to detecting the ventricular tachycardia; and
processing means for determining, during the charging, if the cardiac signal occurring during the charging is monomorphic;
means for terminating the charging of the capacitor in response to the cardiac signal being monomorphic ventricular tachycardia during the charging; and
means for delivering a shock pulse at less than the programmed shock energy.

24. A medical device, comprising:
a sensing module for receiving a cardiac signal;
a therapy delivery module comprising a capacitor and an output circuit; and
a control module coupled to the sensing module and the therapy delivery module and configured to:
detect a tachycardia from the cardiac signal,
initiate charging of the capacitor in response to detecting the tachycardia,
simultaneously monitor a voltage on the capacitor and a morphology of the cardiac signal during the charging; and
control the therapy delivery circuit to deliver a shock pulse at less than a programmed shock energy in response to both the voltage reaching at least a minimum voltage and the morphology of the detected tachycardia being monomorphic.

\* \* \* \* \*